US008052896B2

(12) United States Patent
Kato et al.

(10) Patent No.: US 8,052,896 B2
(45) Date of Patent: Nov. 8, 2011

(54) NANOCARBON FILM AND PRODUCING METHOD THEREOF

(75) Inventors: Takashi Kato, Ashigarakami-gun (JP); Naoyuki Hayashi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 395 days.

(21) Appl. No.: 12/379,492

(22) Filed: Feb. 24, 2009

(65) Prior Publication Data

US 2009/0218549 A1 Sep. 3, 2009

(30) Foreign Application Priority Data

Feb. 28, 2008 (JP) ................................ 2008-047458

(51) Int. Cl.

| | |
|---|---|
| ***H01B 1/00*** | (2006.01) |
| ***H01B 1/04*** | (2006.01) |
| ***H01B 1/06*** | (2006.01) |
| ***C07J 11/00*** | (2006.01) |
| ***B01J 35/00*** | (2006.01) |
| ***B01J 19/08*** | (2006.01) |
| ***H05B 6/00*** | (2006.01) |

(52) U.S. Cl. ... 252/500; 252/502; 252/510; 204/157.15; 204/158.2; 427/457; 427/595

(58) Field of Classification Search .................. 252/500, 252/502, 510; 204/157.15, 158.2; 427/457, 427/595

See application file for complete search history.

(56) References Cited

U.S. PATENT DOCUMENTS

2006/0052509 A1* 3/2006 Saitoh ........................... 524/496
2006/0284538 A1* 12/2006 Harutyunyan ................ 313/311
2007/0258880 A1* 11/2007 Murakoshi ................. 423/447.1

FOREIGN PATENT DOCUMENTS

JP A 2004-345918 12/2004
WO WO 2004/060798 7/2004

OTHER PUBLICATIONS

Colloid Surf. A: Physicochem. Eng. Asp. No. 308, pp. 118 to 122, (2007).
Chemistry Letters, vol. 34 (2005) No. 6, pp. 814 to 815.
Chemistry Letters, vol. 32 (2003) No. 1, pp. 8 to 9.

* cited by examiner

*Primary Examiner* — Randy Gulakowski
*Assistant Examiner* — Jaison Thomas
(74) *Attorney, Agent, or Firm* — SOLARIS Intellectual Property Group, PLLC

(57) ABSTRACT

A nanocarbon film that is produced in such a manner that, after a nanocarbon dispersion containing nanocarbon and a dispersant is used to form a film containing the nanocarbon and the dispersant, an external stimulus is applied to the film to at least partially decompose the dispersant contained in the film. Light irradiation is preferably applied as the external stimulus.

10 Claims, No Drawings

NANOCARBON FILM AND PRODUCING METHOD THEREOF

CROSS REFERENCE TO RELATED APPLICATION

This application claims priority under 35 USC 119 from Japanese patent application No. 2008-047458, the disclosure of which is incorporated herein by reference.

BACKGROUND OF THE INVENTION

1. Field of the Invention

The present invention relates to a nanocarbon film, an electrode using the same and a method of production thereof.

2. Description of the Related Art

In recent years, image displays typical in liquid crystal displays (LCDs), plasma displays (PDPs) and electroluminescence (EL) devices have come to be widely used in various fields such as for televisions, computers and various kinds of mobile devices, which have recently become ubiquitous, and there have been remarkable developments therein. Furthermore, due to increased functionality of solar batteries, there have been demands for increased use thereof as way of reducing the use of fossil energy for environmental reasons.

An electroconductive film is used in display devices and solar batteries such as this. An electroconductive film that uses a metallic material including for instance ITO (indium tin oxide) electroconductive films is generally formed by depositing a metallic material on a glass substrate by use of a vapor phase method such as a vacuum deposition method or a sputtering method.

Furthermore, in display devices such as mobile phones and mobile devices, weight reduction by the gram is forwarded; accordingly, a substrate for a display device is demanded to shift from glass to plastics. When a plastic substrate is introduced, a weight of a display device may be reduced to one half or less of that of a device in which a glass substrate is used and the mechanical strength and impact resistance as well are remarkably improved.

However, when a plastic substrate is substituted for a glass substrate, in the case of forming an ITO electroconductive film thereon, the electroconductive film is liable to exfoliate since its adhesiveness is smaller. In addition to what was mentioned above, a film made of a metallic material such as ITO is usually formed by use of a vapor phase method such as a sputtering method; accordingly, a production unit costs much.

It has been proposed to use nanocarbon such as carbon nanotube as an electroconductive material in place of the metallic material. The nanocarbon is a material capable of forming a thin film having electroconductivity by application and has the likelihood of forming the film at low cost.

As a method of producing carbon nanotubes, various kinds of methods such as an arc discharge method, a laser ablation method and a CVD method are known. However, when these methods are used, carbon impurities such as graphite particles and amorphous carbon may become mixed therewith. As a refining method of the carbon nanotubes, for instance, a method in which UV rays are irradiated to remove carbon impurities has been disclosed (Japanese Patent Application Laid-Open (JP-A) 2004-345918).

When carbon nanotubes are used to form a thin film, the carbon nanotubes are difficult to disperse in a medium such as water. Accordingly, a method has been proposed in which a carbon nanotube dispersion is prepared by adding for instance a dispersant and the dispersion is coated on a substrate to form a thin film (WO2004/060798).

SUMMARY OF THE INVENTION

The present invention has been made in view of the above circumstances and provides a nanocarbon film and a method of production thereof as described below.

According to a first aspect of the invention, a nanocarbon film produced in such a manner that, after a nanocarbon dispersion containing nanocarbon and a dispersant is used to form a film containing the nanocarbon and the dispersant, an external stimulus is applied to the film to at least partially decompose the dispersant contained in the film, is provided.

According to a second aspect of the invention, a nanocarbon film produced in such a manner that, after a nanocarbon dispersion containing nanocarbon and a dispersant is used to form a film containing the nanocarbon and the dispersant, an external stimulus is applied to the film to reduce an electrical resistance value of the film, is provided.

According to a third aspect of the invention, a method of producing a nanocarbon film, including:

providing a nanocarbon dispersion containing nanocarbon and a dispersant on a support;

forming a film containing the nanocarbon and the dispersant from the nanocarbon dispersion provided on the support; and applying an external stimulus to the film to at least partially decompose the dispersant contained in the film, is provided.

According to a fourth aspect of the invention, a method of producing a nanocarbon film, including:

providing a nanocarbon dispersion containing nanocarbon and a dispersant on a support;

forming a film containing the nanocarbon and the dispersant from the nanocarbon dispersion provided on the support; and applying an external stimulus to the film to reduce a resistance value of the film, is provided

DETAILED DESCRIPTION OF THE INVENTION

When a film is formed using a nonocarbon dispersion, a dispersant is incorporated in the film, and therefore there are problems in terms of functions as a conductive film in comparison with nonocarbon alone, for instance, it is difficult to obtain a uniform film, its electroconductivity is low, its adhesion to a substrate is poor and the like.

The present inventors found that when a nanocarbon dispersion containing nanocarbon and a dispersant is used to form a film containing the nanocarbon and the dispersant and thereafter an external stimulus is applied to the film, a nanocarbon film high in the uniformity is formed and an electrical resistance value of the film is reduced. Furthermore, the inventors investigated a reason why the electrical resistance value of the nanocarbon film is reduced by the external stimulus and found that a main reason thereof is in that when the dispersant contained in the nanocarbon film is decomposed, contact among nanocarbons is improved.

Such a nanocarbon film excellent in the film forming property and electroconductivity is preferably produced according to a method that includes:

providing a nanocarbon dispersion containing nanocarbon and a dispersant on a support;

forming a film containing the nanocarbon and the dispersant from the nanocarbon dispersion provided on the support; and applying an external stimulus to the film to reduce an electrical resistance value of the film (or at least partially decomposing the dispersant contained in the film).

<Nanocarbon>

As nanocarbon contained in a nanocarbon film according to the invention, carbon nanotube is preferred in particular from the viewpoint of electroconductivity, film forming property, durability, transparency etc.

As the carbon nanotube, there are a multi-walled carbon nanotube (MWCT) and a single-walled carbon nanotube (SWCT). In the invention, both thereof may be used. These may be used singularly or in a combination thereof.

The single-walled carbon nanotube may be either a semi-conductive carbon nanotube or a metallic carbon nanotube and a mixing ratio thereof is preferably controlled depending on uses therof. When a carbon nanotube film of the invention is formed for use in electrodes, a higher ratio of the metallic carbon nanotube is preferred from the viewpoint of the electroconductivity.

Furthermore, metal or the like may be incorporated in carbon nanotube and peapod nanotube incorporating fullerene may be used.

The carbon nanotubes may be synthesized by means of an arbitrary method such as an arc discharge method, a laser ablation method or a CVD method.

A diameter of the carbon nanotube used in the invention is not particularly restricted. However, the diameter thereof is preferably 0.3 nm or more and 100 nm or less and more preferably 1 nm or more and 30 nm or less from the viewpoints of the durability, transparency, film forming property, electroconductivity etc.

A length of the carbon nanotube used in the invention is neither particularly restricted. However, the length thereof is preferably 0.01 μm or more and 1000 μm or less and more preferably 0.1 μm or more and 100 μm or less from the viewpoints of easiness of production easiness, film forming property, electroconductivity etc.

Examples of the nanocarbon include a carbon nanohorn, a carbon nanocoil and a carbon nanobead other than the carbon nanotube. These as well may be used. When these nanocarbons are used as well, a size thereof is not particularly restricted. However, the length thereof is preferably 0.01 μm or more and 1000 μm or less and more preferably 0.1 μm or more and 100 μm or less from the viewpoints of easiness of production, film forming property, electroconductivity etc.

<Dispersant>

A material that has a function of dispersing nanocarbons in a solvent in a nanocarbon dispersion before a nanocarbon film is formed, and is decomposable when external stimulus such as light irridation is applied after the film is formed, is preferably used as a dispersant. Examples of such a dispersant include polymers, surfactants and low molecule compounds.

Examples of polymers usable as a dispersant include polyvinyl alcohol, polyacrylamide, polystyrene, polystyrene sulfonate, polyphenylene vinylene and DNA. These polymers may be modified in a side chain thereof. As a modified functional group, a π-conjugate site such as pyrene is preferred.

Examples of the low molecule compound usable as the dispersant include amine compounds, porphyrin compounds and pyrene compounds. Specific examples thereof include octadecyl amine, 5,10,15,20-tetrakis(hexadecyloxyphenyl)-21H,23H-porphine, zinc porphyrin and zinc protoporphyrin.

As the surfactant, there are ionic (anionic/cationic/zwitterionic) surfactants and nonionic surfactants, any one of these being used in the invention.

Examples of anionic surfactant include fatty acid salts and cholates as carboxylate and sodium linear alkylbenzene-sulfonate and sodium lauryl sulfate as sulfonate.

Examples of the cationic surfactant include alkyl trimethyl ammonium salt, dialkyldimethyl ammonium salt, and alkylbenzyldimethyl ammonium salt.

Examples of the zwitterionic (amphoteric) surfactant include alkyldimethylamine oxide and alkylcarboxy betaine.

Examples of the nonionic surfactant include polyoxyethylene alkyl ether, fatty acid sorbitan ester, alkyl polyglucoside, fatty acid diethanolamide, and alkylmonoglyceryl ether.

In the invention, a carbon nanotube dispersion obtained by dispersing carbon nanotubes in a medium by use of a surfactant, preferably betaine, is preferably used. In particular, surfactants containing at least one of an ammonium group, a sulfonate group and an oxysulfonate group are preferred since the functions of dispersability and decomposability by an external stimulus can be easily combined. Among surfactants having these groups, compounds represented by formula (A) shown below are particularly preferred.

(A)

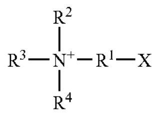

In the formula (A), $R^1$ represents a divalent linkage group, $R^2$, $R^3$ and $R^4$ represent an alkyl group, an aryl group or a heteroaryl group. X represents a dissociative group.

The $R^1$ represents a divalent linkage group and is formed of an atomic group constituted of a carbon atom, a nitrogen atom, a sulfur atom and an oxygen atom. Examples of the divalent linkage group include divalent linkage groups having 0 to 60 carbon atoms constituted by combining one or more selected from an alkylene group having 1 to 20 carbon atoms (such as methylene, ethylene, propylene, butylene, pentylene, cyclohexyl-1,4-diyl), an alkenylene group having 2 to 20 carbon atoms (such as ethenylene), an alkynylene group having 2 to 20 carbon atoms (such as ethynylene), an amide group, an ether group, an ester group, a sulfonamide group, a sulfonate ester group, a ureido group, a sulfonyl group, a sulfinyl group, a thioether group, a carbonyl group, a —NR— group (herein, R represents a hydrogen atom, an alkyl group, or an aryl group), an azo group, an azoxy group, and a heterocyclic divalent group (such as piperazine-1,4-diyl group). Preferable examples thereof include an alkylene group, an alkenylene group, an alkynylene group, an ether group, a thioether group, an amide group, an ester group, a carbonyl group and a combination thereof. These may further have a substituent group. Examples of the substituent group include a group of substituent group V described below.

Group of substituent groups V: a halogen atom (such as chlorine, bromine, iodine or fluorine), a mercapto group, a cyano group, a carboxyl group, a phosphate group, a sulfo group, a hydroxy group, a carbamoyl group having 1 to 10 carbon atoms, preferably 2 to 8 carbon atoms and more preferably 2 to 5 carbon atoms (such as methylcarbamoyl, ethylcarbamoyl or morpholinocarobonyl), a sulfamoyl group having 0 to 10 carbon atoms, preferably 2 to 8 carbon atoms and more preferably 2 to 5 carbon atoms (such as methylsulfamoyl, ethylsulfamoyl or piperidinosulfonyl), a nitro group, an alkoxy group having 1 to 20 carbon atoms, preferably 1 to 10 carbon atoms and more preferably 1 to 8 carbon atoms (such as methoxy, ethoxy, 2-methoxyethoxy or 2-phenylethoxy), an aryloxy group having 6 to 20 carbon atoms, preferably 6 to 12 carbon atoms and more preferably 6 to 10 carbon atoms (such as phenoxy, p-methylphenoxy, p-chlorophenoxy or naphthoxy), an acyl group having 1 to 20 carbon atoms, preferably 2 to 12 carbon atoms and more preferably 2 to 8 carbon atoms (such as acetyl, benzoyl or trichloroacetyl), an acyloxy group having 1 to 20 carbon atoms, preferably 2 to 12 carbon atoms and more preferably 2 to 8 carbon atoms (such as acetyloxy or benzoyloxy), an acylamino group having 1 to 20 carbon atoms, preferably 2 to 12 carbon atoms and more preferably 2 to 8 carbon atoms (such as acetylamino), a sulfonyl group having 1 to 20 carbon atoms, preferably 1 to 10 carbon atoms and more preferably 1 to 8 carbon atoms (such as methanesulfonyl, ethanesulfonyl or benzenesulfonyl), a sulfinyl group having 1 to 20 carbon atoms, preferably 1 to 10 carbon atoms and more preferably 1 to 8 carbon atoms (such as methanesulfinyl, ethanesulfinyl or benzenesulfinyl), a substituted or unsubstituted amino group having 1 to 20 carbon atoms, preferably 1 to 12 carbon atoms and more preferably 1 to 8 carbon atoms (such as amino, methylamino, dimethylamino, benzylamino, anilino, diphenylamino, 4-methylphenylamino, 4-ethylphenylamino, 3-n-propylphenylamino, 4-n-propylphenylamino, 3-n-butylphenylamino, 4-n-butylphenylamino, 3-n-pentylphenylamino, 4-n-pentylphenylamino, 3-trifluoromethylphenylamino, 4-trifluoromethylphenylamino, 2-pyridylamino, 3-pyridylamino, 2-thiazolylamino, 2-oxazolylamino, N,N-methylphenylamino or N,N-ethylphenylamino), an ammonium group having 0 to 15 carbon atoms, preferably 3 to 10 carbon atoms and more preferably 3 to 6 carbon atoms (such as trimethylammonium or triethylammonium), a hydrazino group having 0 to 15 carbon atoms, preferably 1 to 10 carbon atoms and more preferably 1 to 6 carbon atoms (such as trimethylhydrazino group), a ureido group having 1 to 15 carbon atoms, preferably 1 to 10 carbon atoms and more preferably 1 to 6 carbon atoms (such as ureido group, N,N-dimethylureido group), an imide group having 1 to 15 carbon atoms, preferably 1 to 10 carbon atoms and more preferably 1 to 6 carbon atoms (such as succineimide group), an alkylthio group having 1 to 20 carbon atoms, preferably 1 to 12 carbon atoms and more preferably 1 to 8 carbon atoms (such as methylthio, ethylthio or propylthio), an arylthio group having 6 to 80 carbon atoms, preferably 6 to 40 carbon atoms and more preferably 6 to 30 carbon atoms (such as phenylthio, p-methylphenylthio, p-chlorophenylthio, 2-pyridylthio, 1-naphthylthio, 2-naphthylthio, 4-propylcyclohexyl-4'-biphenylthio, 4-butylcyclohexyl-4'-biphenylthio, 4-pentylcyclohexyl-4'-biphenylthio or 4-propylphenyl-2-ethynyl-4'-biphenylthio), a heteroarylthio group having 1 to 80 carbon atoms, preferably 1 to 40 carbon atoms and more preferably 1 to 30 carbon atoms (such as 2-pyridylthio, 3-pyridylthio, 4-pyridylthio, 2-quinolylthio, 2-furylthio or 2-pyrolylthio), an alkoxycarbonyl group having 2 to 20 carbon atoms, preferably 2 to 12 carbon atoms and more preferably 2 to 8 carbon atoms (such as methoxycarbonyl, ethoxycarbonyl or 2-benzyloxycarbonyl), an aryloxycarbonyl group having 6 to 20 carbon atoms, preferably 6 to 12 carbon atoms and more preferably 6 to 10 carbon atoms (such as phenoxycarbonyl), an unsubstituted alkyl group having 1 to 18 carbon atoms, preferably 1 to 10 carbon atoms and more preferably 1 to 5 carbon atoms (such as methyl, ethyl, propyl, butyl, pentyl, or octyl), a substituted alkyl group having 1 to 18 carbon atoms, preferably 1 to 10 carbon atoms and more preferably 1 to 5 carbon atoms (such as hydroxymethyl, trifluoromethyl, benzyl, carboxyethyl, ethoxycarbonylmethyl, or acetylaminomethyl, and herein an unsaturated hydrocarbon group having 2 to 18 carbon atoms, preferably 3 to 10 carbon atoms and more preferably 3 to 5 carbon atoms (such as vinyl group, ethynyl group, 1-cyclohexenyl group, benzylidyne group or benzylidene group) as well is regarded as the substituted alkyl group), a substituted or unsubstituted aryl group having 6 to 20 carbon atoms, preferably 6 to 15 carbon atoms and more preferably 6 to 10 carbon atoms (such as phenyl, naphthyl, p-carboxyphenyl, p-nitrophenyl, 3,5-dichlorophenyl, p-cyanophenyl, m-fluorophenyl, p-tolyl, 4-propylcyclohexyl-4'-biphenyl, 4-butylcyclohexyl-4'-biphenyl, 4-pentylcyclohexyl-4'-biphenyl, 4-propylphenyl-2-ethynyl-4'-biphenyl), and a substituted or unsubstituted heteroaryl group having 1 to 20 carbon atoms, preferably 2 to 10 carbon atoms and more preferably 4 to 6 carbon atoms (such as pyridyl, 5-methylpyridyl, thienyl, furyl, morpholino or tetrahydrofuryl).

The group V of substituent groups may have a structure formed by condensing benzene rings or naphthalene rings. Furthermore, the substituent groups may be further substituted with a substituent group given in the explanation of V described above.

In the formula (A), $R^2$, $R^3$ and $R^4$ each represent an alkyl group, an aryl group or a heteroaryl group. The alkyl group is an alkyl group having preferably 1 to 60 carbon atoms, more preferably 1 to 50 carbon atoms and still more preferably 1 to 40 carbon atoms. Specific examples thereof include methyl group, t-butyl group, t-octyl group, 2-ethylhexyl group, cyclohexyl group, n-hexadecyl group, 3-dodecyloxypropyl group, 3-(2',4'-di-tert-pentylphenoxy)propyl group and benzyl group. The aryl group is an aryl group having preferably 6 to 60 carbon atoms, more preferably 6 to 50 carbon atoms and still more preferably 6 to 40 carbon atoms. Specific examples thereof include phenyl group, 1-naphthyl group, p-tolyl group, o-tolyl group, 4-methoxyphenyl group, 4-hexadecyloxyphenyl group, 3-pentadecylphenyl group, 2,4-di-tert-pentylphenyl group, 8-quinolyl group, and 5-(1-dodecyloxycarbonylethoxycarbonyl)-2-chlorophenyl group. The heteroaryl group is preferably 5 to 8-membered heteroaryl group containing at least one hetero atom selected from a group of N, S, O and Se. Specific examples thereof include 4-pyridyl group, 2-furyl group, 2-pyrrole group, 2-thiazolyl group, 3-thiazolyl group, 2-oxazolyl group, 2-imidazolyl group, triazolyl group, tetrazolyl group, benzotriazolyl group, 2-quinolyl group and 3-quinolyl group.

Specific examples of preferable surfactants include 3-(3-colamidpropyl)dimethylamino-2-hydroxy-1-propane sulfonate, distearoylphosphatidylcholine, dimyristoylphosphatidylcholine, dipalmitorylphosphatidylcholine, 3-[(3-colamidpropyl)dimethylamino]-propane sulfonic acid and N,N-bis(3-D-gulconamidepropyl)-colamid.

Furthermore, dissociative surfactants having a benzyl group are preferred. Specific examples thereof preferably include surfactants described in, for instance, Chemistry Letters, Vol. 32 (2003) No. 1, pp. 8 to 9; Chemistry Letters, Vol. 34 (2005) No. 6, pp. 814 to 815; and Colloid Surf. A: Physicochem. Eng. Asp. No. 308, pp. 118 to 122, (2007).

Structural formulas of dispersants usable in the invention are shown below without restricting thereto.

(1)

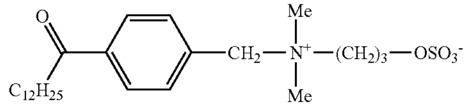

-continued (2)

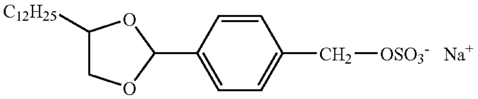

(3)

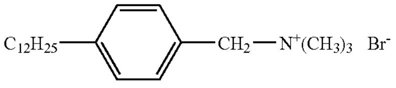

(4)

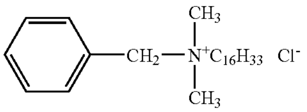

(5)

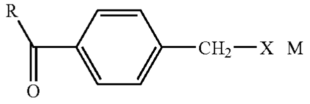

R = alkyl chain of C1 through C12
M = counter ion
$X = N^+(CH_3)_3$, $OSO_3$ (6)

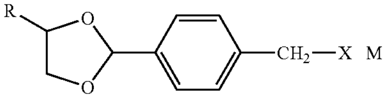

R = alkyl chain of C1 through C12
M = counter ion
$X = N^+(CH_3)_3$, $OSO_3^-$ (7)

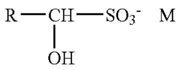

R = alkyl chain of C1 through C12
M = counter ion

The nanocarbon and dispersant such as mentioned above are added in a solvent to prepare a nanocarbon dispersion. Water is preferred as a solvent and an organic solvent such as alcohol as well may be used. A dispersion where the nanocarbon is dispersed is prepared, for instance, in such a manner that a predetermined amount of nanocarbon is added under agitation in an aqueous solution where a predetermined amount of dispersant is added in advance. An amount of the nanocarbon in the nanocarbon dispersion may be determined in accordance with target electroconductivity, transparency and the like. However, it is preferably in the range of 0.001 to 100,000 mg/L, more preferably in the range of 0.01 to 10,000 mg/L and particularly preferably in the range of 0.1 to 10,000 mg/L from the viewpoint of the film forming property.

On the other hand, an amount of the dispersant in the nanocarbon dispersion is, although dependent on the kind of the dispersant and the content of the nanocarbon, usually preferably in the range of 0.00001 to 1000 mM, more preferably in the range of 0.0001 to 100 mM and particularly in the range of 0.001 to 100 mM.

As a method of preparing a dispersion, any one of known methods may be used. Examples of known dispersion methods include a jaw crusher method, an ultra-centrifugal crushing method, a cutting mill method, an automatic mortar method, a disc mill method, a ball mill method and a ultrasonic dispersion method.

<Other Components>

In the nanocarbon dispersion, other than the nanocarbon, dispersant and solvent, lithium hydroxide, ammonium persulfate and a UV-absorbent may be added to improve the dispersion stability; inorganic fine particles, polymer fine particles and a silane coupling agent may be added to improve the film strength; and a fluorinated compound, in particular, a fluorinated surfactant may be added to improve the transparency by reducing the refractive index.

When the nanocarbon dispersion containing the nanocarbon and the dispersant such as mentioned above is coated on a support and the nanocarbon dispersion coated on the support is dried, a film containing the nanocarbon and the dispersant is formed.

<Support>

As the support, one that allows forming a film by coating a nanocarbon dispersion thereon and is not or slightly adversely affected by an external stimulus applied when the dispersant is decomposed is selected depending on uses after a nanocarbon film is formed or the like. In the case where the nanocarbon film is formed as an electrode of a display device such as a LCD, a glass substrate or plastic substrate is preferably used. Furthermore, a metal substrate provided with an insulating film between the nanocarbon film and the substrate may be used. The support is not restricted to a plate-shaped support. For instance, one having a curved surface or an irregular surface may be selected depending on uses. Still furthermore, the support may be pre-treated as required. For instance, an adhesive layer may be formed on a support to improve the adhesiveness with the nanocarbon film.

Substrates made of glass, transparent ceramics, metals, plastic film or the like may be used as the support in the invention. The glass and transparent ceramic are inferior in the flexibility to the metal and plastics film. When the price is compared between the metal and plastic film, the plastic film is cheaper and has the flexibility. From these viewpoints, as the support of the invention, the plastic film is preferred and a polyester resin (hereinafter, appropriately referred to as "polyester") is particularly preferred. As the polyester, linear saturated polyester synthesized from aromatic dibasic acid or an ester-forming derivative thereof and diol or an ester-forming derivative thereof is preferred.

Specific examples of polyester usable in the invention include polyethylene terephthalate, polyethylene isophthalate, polyethylene naphthalate, polybutylene terephthalate, poly(1,4-cyclohexylenedimethylene terephthalate) and polyethylene-2,6-phthalenedicarboxylate. Among these, polyethylene terephthalate and polyethylene naphthalate are preferred from the view points of the easy availability, economic efficiency and effect.

As a material of the film, as long as it does not disturb the advantages of the invention, copolymers thereof or blends with other resin at a small ratio as well may be used.

Furthermore, in the polyester film, a small amount of inorganic or organic fine particles, for instance, inorganic fillers such as titanium oxide, calcium carbonate, silica, barium sulfate or silicon or organic fillers such as acryl, benzoguanamine, Teflon (registered trade mark) or epoxy may be added to improve slip property and adhesiveness improver or an antistatic agent such as polyethylene glycol (PEG) and sodium dodecylbenzene sulfonate may be added.

The polyester film usable in the invention may be formed in such a manner that the polyester resin such as mentioned above is melt-extruded as a film, followed by orientating and crystallizing by longitudinal and lateral biaxial stretching, further followed by crystallizing by heat treatment. The producing method and conditions of the films are used by appropriately selecting from known methods and conditions.

A thickness of the polyester film used herein may be selected and used appropriately depending on uses of the film without particular restriction. However, the thickness thereof is generally preferred to be from 5 to 500 μm.

As the adhesion layer in the invention, a configuration containing a styrene-butadiene copolymer (hereinafter, appropriately abbreviated as "SBR") or an aqueous urethane resin and a crosslinking agent is preferred. The SBR means a copolymer mainly made of styrene and butadiene and a copolymer copolymerized with other component as required. With respect to the copolymer, it is known that copolymers having various physical properties are obtained by controlling a content ratio of styrene and butadiene.

In the case of forming an adhesion layer, a styrene-butadiene copolymer is preferably latex. Specifically, commercially available products such as NIPOL (trade name, manufactured by ZEON CORPORATION), NAUGATEX (trade name, manufactured by Sumitomo Naugatuck Co., Ltd.), CROSSLENE (trade name, manufactured by Takeda Pharmaceutical Company Limited), ASAHI DOW LATEX (trade name, manufactured by Asahi-Dow Co., Ltd.) and others available from DIC Corporation and foreign manufacturers may be used.

In the case of the latex, a particle diameter of dispersed particles is preferably 5 μm or less, more preferably 1 μm or less and still more preferably 0.2 μm or less. In the case where a particle diameter is large, there are problems in that particles tend to flocculate in a coating step and the transparency and glossiness of the film may be deteriorated. In the case where a thickness of a coating layer is necessary to be made thinner, the particle diameter is necessarily made smaller accordingly.

A content ratio of styrene/butadiene in the styrene-butadiene copolymer in the adhesion layer is preferably substantially from 50/50 to 80/20. A ratio of SBR contained in the latex is preferably from 30 to 50% by weight as a solid content.

Furthermore, a crosslinking agent is added to the adhesion layer to improve the physical property of the SBR. A triazine crosslinking agent is preferably used as a crosslinking agent used herein.

When an external stimulus is used to decompose the dispersant, a support as well is exposed to the external stimulus. Accordingly, the support preferably contains an additive capable of inhibiting the external stimulus from causing an adverse affect. For instance, when a resin film is used as a support and UV-ray is irradiated as the external stimulus to decompose the dispersant contained in the nanocarbon film, it is preferred that a resin film containing a UV-absorbent is used and UV-ray is irradiated from a surface different from a side of the support. Examples of preferable UV-absorbent include an oxazole absorbent, a triazine absorbent, a stilbene absorbent and a coumarin absorbent.

<Film Formation>

A method of forming a film is not particularly restricted. A coating method may be selected from known coating methods such as an extrusion die coat method, a blade coat method, a bar coat method, a screen printing method, a roll coat method and a curtain coat method. A nanocarbon dispersion is provided on a support so that a thickness of a dry film may be a thickness desired corresponding to target electroconductivity and then dried. A drying unit may be used as required. For instance, after a nanocarbon dispersion is coated on a support, a hot air is blown to rapidly vaporize a solvent, thereby a nanocarbon film is formed.

In the case of forming a transparent electrode from the carbon nanotube, its electrical resistance value and light transmittance are important. In this case, a film thickness may be controlled while considering the concentration (density) of the carbon nanotube. For instance, in the case of transparent electrode for display devices such as LCDs, PDPs and ELs, a preferable electrical resistance value is in the range of 0.001 to 100,000Ω/□ and more preferably in the range of 0.1 to 10,000Ω/□. The transparency of the transparent electrode according to the invention means that the light transmittance at 550 nm is in the range of 10 to 100%. The transmittance is preferably in the range of 20 to 100% and more preferably in the range of 50 to 100%.

<External Stimulus>

After a nanocarbon dispersion is coated on a support and thereby a film is formed thereon, an external stimulus is applied to the film to at least partially decompose the dispersant contained in the film. Examples of the external stimulus include heat, light, an electric field, a magnetic field, pressure, a chemical substance and an ultrasonic wave. The external stimulus may be selected therefrom depending on the kind of the dispersant. However, light irradiation is preferred from the viewpoint of being capable of uniformly and inexpensively irradiating a large area. The light irradiation has only to decompose the dispersant contained in the nanocarbon film. A xenon light source, a super-xenon light source, a laser light source, a mercury lamp light source and a tungsten lamp light source are preferred and a xenon lamp light source and a super xenon light source are more preferred from the viewpoint of a decomposition action to the dispersant.

In the case of a xenon light source being used, a light irradiation dose may be selected in accordance with the kind of the dispersant etc. However, the irradiation dose is usually preferably from 10,000 to 200,000 lux and more preferably from 100,000 to 200,000 lux from the viewpoint of decomposition productivity to the dispersant. An irradiation time is neither particularly restricted. The irradiation time may be set in accordance with the kind of dispersant and uses of the nanocarbon films. However, the irradiation time is preferably set in the range of 1 min to 200 hr and more preferably from 1 hr to 50 hr from the viewpoint of assuredly decomposing the dispersant and the productivity. Furthermore, a temperature (decomposition temperature) when the dispersant is decomposed by irradiating light is preferably set at a temperature of room temperature or more to 100° C. or less from the viewpoint of not deteriorating the performance of the support and carbon.

If the dispersant in the nanocarbon film is partially decomposed, the resistance value thereof is reduced. Accordingly, the dispersant is not necessarily decomposed completely and may be decomposed by applying the external stimulus in accordance with a target resistance value. It is thought that when light having a specified wavelength is irradiated as the external stimulus, the dispersant present around the carbon nanotubes is decomposed to increase a contact area between respective carbon nanotubes, and thereby the resistance value of a carbon nanotube thin film is reduced. Whether the dispersant is decomposed or not may be confirmed by, in addition to a method where the resistance value of the nanocarbon film is measured before and after the application of the external stimulus, a method that uses IR to check whether or not a peak wavelength of a specified functional group of the dispersant is present.

In this manner, the nanocarbon film according to the invention becomes a film high in electroconductivity when the resistance value is reduced by the external stimulus. Accordingly, the nanocarbon film of the invention is preferably applied as a transparent electrode of thin displays such as LCDs, PDPs and ELs, solar batteries and touch panels.

EXAMPLES

Hereinafter, examples of the present invention will be described. However, the invention is not restricted to examples shown below.

Example 1

(A) Preparation of Carbon Nanotube Dispersion

In an aqueous solution (2 L) of 5 mM of 3-(3-colamidpropyl)dimethylamino-2-hydroxy-1-propane sulfonic acid to which 0.1 M of lithium hydroxide and 0.05 M of ammonium persulfate are added, 2.0 g of multi-walled carbon nanotube (manufactured by Aldrich) is added at room temperature under agitation. The resulted solution is dispersed for 10 min by use of an ultrasonic dispersing device, followed by heating and agitating at 60° C., thereby a solution in which carbon nanotubes are uniformly dispersed is obtained.

(B) Film Formation of Carbon Nanotube Thin Film

A glass substrate is used as a support. A die coater that uses an extrusion coating head is used as a coating unit. A thickness of the wet coating film is controlled so that a film thickness after drying may be 100 nm. A hot air circulating dryer is used as a drying unit. A temperature of the hot air is set at 100° C. A roller which has a diameter of 200 mm and on a surface of which a layer of silicone rubber having rubber hardness of 90 is formed is used as a nip roller.

(C) Light Irradiation

Light (100,000 lux with a xenon lamp source) is irradiated to the resulted carbon nanotube thin film for 48 hr. The light transmittance and resistance value of the carbon nanotube thin film are measured before and after the light irradiation. The light transmittance is measured by use of a UV/VIS spectrometer (trade name: U2400, manufactured by Shimadzu Corporation) and the resistance value is measured by use of a Loresta RESISTANCE METER (trade name, manufactured by Mitsubishi Chemical Corporation).

Before irradiation of light, the light transmittance at 550 nm is 80% and the resistance value is 1200Ω/□ and, after irradiation of light, the light transmittance is 80% and the resistance value is 660Ω/□, that is, it is confirmed that the electroconductivity is improved without lowering the light transmittance. Furthermore, the resulted electroconductive film is confirmed to be high in the adhesiveness.

On the other hand, in a case where a surfactant is not used, that is, a comparative example, a carbon nanotube thin film is difficult to dispose uniformly on a support and a film high in the light transmittance and low in the resistance value is not obtained. Furthermore, it is confirmed that the adhesiveness between the carbon nanotube thin film and the support is low.

Examples 2 through 5

Carbon nanotube dispersions are prepared in a procedure similar to that of example 1 except that in place of 3-(3-colamid propyl)dimethylamino-2-hydroxy-1-propane sulfonate used as the dispersant in example 1, compounds (1), (2), (3) and (4) shown below are used respectively and films are prepared therefrom.

(1)

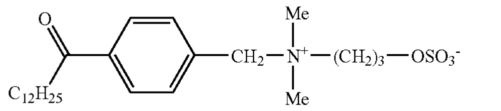

(2)

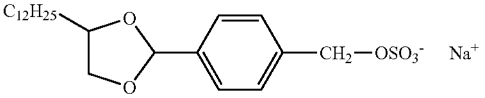

(3)

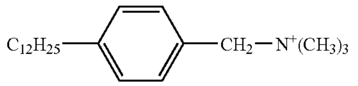

(4)

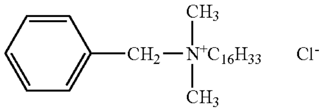

A film is formed in a manner similar to example 1 with each of the carbon nanotube dispersions, followed by irradiating light. The light transmittance and resistance value of the film are measured before and after irradiation of light and it is confirmed that in all cases the resistance value is lowered without reducing the light transmittance.

Example 6

A carbon nanotube thin film formed in a procedure similar to example 1 is irradiated by a super-xenon light source (170,000 lux, 36 hr irradiation) instead of a xenon light source and a reduction in the resistance value similar to example 1 is observed.

Examples 7 through 10

Carbon nanotube thin films each prepared in a procedure similar to each of examples 2 through 5 are subjected to light irradiation by use of a super-xenon light source (170,000 lux, 36 hr irradiation) instead of a xenon light source. The resistance value of each of examples is observed to reduce in a manner similar to examples 2 through 5, respectively.

The nanocarbon film according to the invention and a method of production thereof are described above. However, the invention is not restricted to the exemplary embodiments and examples described above. For instance, when a transparent electrode that uses a nanocarbon film according to the invention is formed, a photolithography method may be used to form a pattern, as required. Furthermore, the nanocarbon film according to the invention may be applied as not only the transparent electrode but also various kinds of functional materials.

The foregoing description of the embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

All publications, patent applications, and technical standards mentioned in this specification are herein incorporated by reference to the same extent as if each individual publication, patent application, or technical standard was specifically and individually indicated to be incorporated by reference.

What is claimed is:

1. A method of producing a nanocarbon film, comprising:

providing a nanocarbon dispersion containing nanocarbon and a dispersant on a support;

forming a film containing the nanocarbon and the dispersant from the nanocarbon dispersion provided on the support; and applying an external stimulus to the film to at least partially decompose the dispersant contained in the film, wherein light irradiation is applied as the external stimulus, and wherein the light irradiation is performed by use of a xenon light source or a super xenon light source.

2. The method of producing of a nanocarbon film of claim 1, wherein the dispersant is a surfactant.

3. The method of producing of a nanocarbon film of claim 1, wherein the surfactant is betaine.

4. The method of producing of a nanocarbon film of claim 3, wherein the betaine is a compound represented by the following Formula (A):

(A)

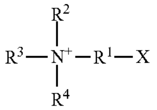

wherein, in Formula (A), R2, R3 and R4 each independently represent an alkyl group, an aryl group or a heteroaryl group; $R^1$ represents an alkylene group having 1 to 20 carbon atoms, an alkenylene group having 2 to 20 carbon atoms, or an alkynylene group having 2 to 20 carbon atoms; $R^1$, R2, R3 and R4 may each independently have further a substituent V; V represents an aryl group, a hydroxyl group, an acyl group, an acylamino group or an alkoxy group; and X represents $—OSO_3^-$ or $—SO_3^-$.

5. The method of producing of a nanocarbon film of claim 2, wherein the surfactant is a compound represented by any one of the following Formulae (1) to (7)

(1)

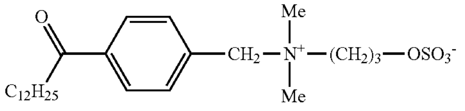

(2)

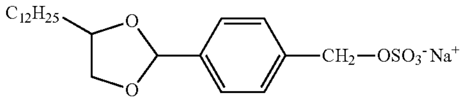

(3)

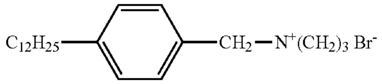

(4)

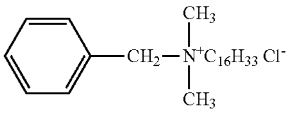

(5)

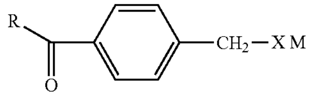

R = alkyl chain of C1 through C12
M = counter ion
$X = N^+(CH_3)_3, OSO_3$ (6)

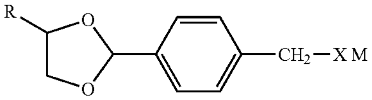

R = alkyl chain of C1 through C12
M = counter ion
$X = N^+(CH_3)_3, OSO_3^-$

-continued (7)

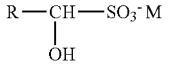

R = alkyl chain of C1 through C12
M = counter ion.

6. The method of producing of a nanocarbon film of claim 2, wherein the surfactant is 3-(3-colamid propyl)dimethylamino-2-hydroxy-1-propane sulfonic acid, or a compound represented by any one of the following Formulae (1) to (4)

(1)

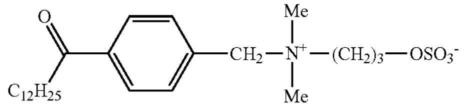

(2)

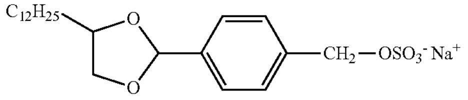

(3)

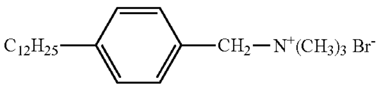

(4)

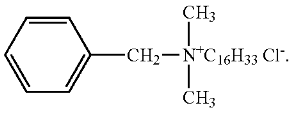

7. The method of producing of a nanocarbon film of claim 1, wherein the nanocarbon is a single-walled carbon nanotube or a multi-walled carbon nanotube.

8. The method of producing of a nanocarbon film of claim 1, wherein the support is a glass substrate or a resin film substrate.

9. The method of producing of a nanocarbon film of claim 1, wherein the support contains a UV absorbent.

10. A method of producing a nanocarbon film, comprising:

providing a nanocarbon dispersion containing nanocarbon and a dispersant on a support;

forming a film containing the nanocarbon and the dispersant from the nanocarbon dispersion provided on the support; and applying an external stimulus to the film to reduce a resistance value of the film wherein light irradiation is applied as the external stimulus, and wherein the light irradiation is performed by use of a xenon light source or a super xenon light source.

* * * * *